(12) United States Patent
Reicher et al.

(10) Patent No.: US 8,457,990 B1
(45) Date of Patent: *Jun. 4, 2013

(54) SMART PLACEMENT RULES

(75) Inventors: Murray A. Reicher, Rancho Santa Fe, CA (US); Cole A. Genovese, Encinitas, CA (US); Carol G. Sloyer, La Jolla, CA (US); Thomas J. Edwards, San Diego, CA (US)

(73) Assignee: DR Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/118,085

(22) Filed: May 27, 2011

Related U.S. Application Data

(63) Continuation of application No. 11/942,674, filed on Nov. 19, 2007, now Pat. No. 7,953,614.

(60) Provisional application No. 60/867,071, filed on Nov. 22, 2006.

(51) Int. Cl.
*G06Q 10/00* (2012.01)

(52) U.S. Cl.
USPC .................................................. 705/3; 705/2

(58) Field of Classification Search
USPC ............................................................ 705/3
See application file for complete search history.

(56) References Cited

U.S. PATENT DOCUMENTS

| | | | |
|---|---|---|---|
| 4,672,683 A | 6/1987 | Matsueda | |
| 5,123,056 A | 6/1992 | Wilson | |
| 5,431,161 A | 7/1995 | Ryals et al. | |
| 5,452,416 A | 9/1995 | Hilton et al. | |
| 5,542,003 A | 7/1996 | Wofford | |
| 5,734,915 A | 3/1998 | Roewer | |
| 5,740,267 A | 4/1998 | Echerer et al. | |
| 5,779,634 A | 7/1998 | Ema et al. | |
| 5,852,646 A | 12/1998 | Klotz et al. | |
| 5,926,568 A | 7/1999 | Chaney et al. | |

(Continued)

FOREIGN PATENT DOCUMENTS

WO WO 2007/131157 11/2007

OTHER PUBLICATIONS

Crowley, Rebecca et al., *Development of Visual Diagnostic Expertise in Pathology: an Information-processing Study*, Jan. 2003, Journal of the American medical Informatics Association, vol. 10, No. 1, pp. 39-51.

(Continued)

*Primary Examiner* — Hiep V Nguyen
(74) *Attorney, Agent, or Firm* — Knobbe Martens Olson & Bear, LLP

(57) ABSTRACT

A smart placement module determines components of received medial data, such as medical reports and image montages, to forward to one or more secondary location, such as an EMR system, based on smart placement rules that are established by a user that receives the medical data, such as a referring doctor. Thus, the smart placement module decreases or removes the need for the receiving user to manually select and transfer certain medical data for storage at the EMR system. Accordingly, the receiving user, and other authorized EMR system users, may have prompt access to the medical data via their respective connections to the EMR system. In one embodiment, the smart placement module transmits a patient identification file that is usable by the receiving EMR system to allow the EMR system to associate received medical data with other data regarding a respective patient.

18 Claims, 4 Drawing Sheets

U.S. PATENT DOCUMENTS

| | | | |
|---|---|---|---|
| 5,954,650 | A | 9/1999 | Saito et al. |
| 5,976,088 | A | 11/1999 | Urbano et al. |
| 5,987,345 | A | 11/1999 | Engelmann et al. |
| 5,995,644 | A | 11/1999 | Lai et al. |
| 6,115,486 | A | 9/2000 | Cantoni |
| 6,151,581 | A | 11/2000 | Kraftson et al. |
| 6,175,643 | B1 | 1/2001 | Lai et al. |
| 6,185,320 | B1 | 2/2001 | Bick et al. |
| 6,304,667 | B1 | 10/2001 | Reitano |
| 6,347,329 | B1 | 2/2002 | Evans |
| 6,351,547 | B1 | 2/2002 | Johnson et al. |
| 6,424,996 | B1 | 7/2002 | Killcommons et al. |
| 6,438,533 | B1 | 8/2002 | Spackman et al. |
| 6,463,169 | B1 | 10/2002 | Ino et al. |
| 6,532,299 | B1 | 3/2003 | Sachdeva et al. |
| 6,532,311 | B1 | 3/2003 | Pritt |
| 6,556,695 | B1 | 4/2003 | Packer et al. |
| 6,563,950 | B1 | 5/2003 | Wiskott et al. |
| 6,574,629 | B1 | 6/2003 | Cooke, Jr. et al. |
| 6,577,753 | B2 | 6/2003 | Ogawa |
| 6,603,494 | B1 | 8/2003 | Banks et al. |
| 6,630,937 | B2 | 10/2003 | Kallergi et al. |
| 6,678,764 | B2 | 1/2004 | Parvelescu et al. |
| 6,697,506 | B1 | 2/2004 | Qian et al. |
| 6,775,402 | B2 | 8/2004 | Bacus et al. |
| 6,778,689 | B1 | 8/2004 | Aksit et al. |
| 6,820,100 | B2 | 11/2004 | Funahashi |
| 6,829,377 | B2 | 12/2004 | Milioto |
| 6,864,794 | B2 | 3/2005 | Betz |
| 6,886,133 | B2 | 4/2005 | Bailey et al. |
| 6,891,920 | B1 | 5/2005 | Minyard et al. |
| 6,917,696 | B2 | 7/2005 | Soenksen |
| 6,996,205 | B2 | 2/2006 | Capolunghi et al. |
| 7,022,073 | B2 | 4/2006 | Fan et al. |
| 7,027,633 | B2 | 4/2006 | Foran et al. |
| 7,031,846 | B2 | 4/2006 | Kaushikkar et al. |
| 7,043,474 | B2 | 5/2006 | Mojsilovic et al. |
| 7,050,620 | B2 | 5/2006 | Heckman |
| 7,092,572 | B2 | 8/2006 | Huang et al. |
| 7,103,205 | B2 | 9/2006 | Wang et al. |
| 7,106,479 | B2 | 9/2006 | Roy et al. |
| 7,110,616 | B2 | 9/2006 | Ditt et al. |
| 7,113,186 | B2 | 9/2006 | Kim et al. |
| 7,149,334 | B2 | 12/2006 | Dehmeshki |
| 7,155,043 | B2 | 12/2006 | Daw |
| 7,170,532 | B2 | 1/2007 | Sako |
| 7,174,054 | B2 | 2/2007 | Manber et al. |
| 7,209,149 | B2 | 4/2007 | Jogo |
| 7,212,661 | B2 | 5/2007 | Samara et al. |
| 7,218,763 | B2 | 5/2007 | Belykh et al. |
| 7,224,852 | B2 | 5/2007 | Lipton et al. |
| 7,260,249 | B2 | 8/2007 | Smith |
| 7,263,710 | B1 | 8/2007 | Hummell et al. |
| 7,272,610 | B2 | 9/2007 | Torres |
| 7,412,111 | B2 | 8/2008 | Battle et al. |
| 7,450,747 | B2 | 11/2008 | Jabri et al. |
| 7,526,114 | B2 | 4/2009 | Seul et al. |
| 7,545,965 | B2 | 6/2009 | Suzuki et al. |
| 7,583,861 | B2 | 9/2009 | Hanna et al. |
| 7,613,335 | B2 | 11/2009 | McLennan et al. |
| 7,634,121 | B2 | 12/2009 | Novatzky et al. |
| 7,636,413 | B2 | 12/2009 | Toth |
| 7,660,488 | B2 | 2/2010 | Reicher et al. |
| 7,787,672 | B2 | 8/2010 | Reicher et al. |
| 7,885,440 | B2 | 2/2011 | Fram et al. |
| 7,920,152 | B2 | 4/2011 | Fram et al. |
| 7,953,614 | B1 | 5/2011 | Reicher |
| 7,970,625 | B2 | 6/2011 | Reicher et al. |
| 8,019,138 | B2 | 9/2011 | Reicher et al. |
| 8,094,901 | B1 | 1/2012 | Reicher et al. |
| 8,217,966 | B2 | 7/2012 | Fram et al. |
| 8,244,014 | B2 | 8/2012 | Murray et al. |
| 2001/0016822 | A1 | 8/2001 | Bessette |
| 2001/0042124 | A1 | 11/2001 | Barron |
| 2002/0016718 | A1 | 2/2002 | Rothschild et al. |
| 2002/0021828 | A1 | 2/2002 | Papier et al. |
| 2002/0044696 | A1 | 4/2002 | Sirohey et al. |
| 2002/0073429 | A1 | 6/2002 | Beane et al. |
| 2002/0081039 | A1 | 6/2002 | Funahashi |
| 2002/0091659 | A1 | 7/2002 | Beaulieu et al. |
| 2002/0103673 | A1 | 8/2002 | Atwood |
| 2002/0103827 | A1 | 8/2002 | Sesek |
| 2002/0106119 | A1 | 8/2002 | Foran et al. |
| 2002/0110285 | A1 | 8/2002 | Wang et al. |
| 2002/0164063 | A1 | 11/2002 | Heckman |
| 2002/0180883 | A1 | 12/2002 | Tomizawa et al. |
| 2002/0188637 | A1 | 12/2002 | Bailey et al. |
| 2003/0005464 | A1 | 1/2003 | Gropper et al. |
| 2003/0028402 | A1 | 2/2003 | Ulrich et al. |
| 2003/0036087 | A1 | 2/2003 | Kaushikkar et al. |
| 2003/0037054 | A1 | 2/2003 | Dutta et al. |
| 2003/0053668 | A1 | 3/2003 | Ditt et al. |
| 2003/0065613 | A1 | 4/2003 | Smith |
| 2003/0115083 | A1 | 6/2003 | Masarie et al. |
| 2003/0123717 | A1 | 7/2003 | Bacus et al. |
| 2003/0185446 | A1 | 10/2003 | Huang et al. |
| 2003/0190062 | A1 | 10/2003 | Noro et al. |
| 2003/0195416 | A1 | 10/2003 | Toth |
| 2003/0204420 | A1 | 10/2003 | Wilkes et al. |
| 2004/0008900 | A1 | 1/2004 | Jabri et al. |
| 2004/0024303 | A1 | 2/2004 | Banks et al. |
| 2004/0068170 | A1 | 4/2004 | Wang et al. |
| 2004/0086163 | A1 | 5/2004 | Moriyama et al. |
| 2004/0088192 | A1 | 5/2004 | Schmidt et al. |
| 2004/0101191 | A1 | 5/2004 | Seul et al. |
| 2004/0114714 | A1 | 6/2004 | Minyard et al. |
| 2004/0141661 | A1 | 7/2004 | Hanna et al. |
| 2004/0143582 | A1 | 7/2004 | Vu |
| 2004/0151374 | A1 | 8/2004 | Lipton et al. |
| 2004/0161139 | A1 | 8/2004 | Samara et al. |
| 2004/0161164 | A1 | 8/2004 | Dewaele |
| 2004/0165791 | A1 | 8/2004 | Kaltanji |
| 2004/0170312 | A1 | 9/2004 | Soenksen |
| 2004/0197015 | A1 | 10/2004 | Fan et al. |
| 2004/0243435 | A1 | 12/2004 | Williams |
| 2004/0254816 | A1 | 12/2004 | Myers |
| 2004/0264753 | A1 | 12/2004 | Capolunghi et al. |
| 2005/0027570 | A1 | 2/2005 | Maier et al. |
| 2005/0036668 | A1 | 2/2005 | McLennan et al. |
| 2005/0043970 | A1 | 2/2005 | Hsieh |
| 2005/0063612 | A1 | 3/2005 | Manber et al. |
| 2005/0065424 | A1 | 3/2005 | Shah et al. |
| 2005/0108058 | A1 | 5/2005 | Weidner et al. |
| 2005/0114178 | A1 | 5/2005 | Krishnamurthy et al. |
| 2005/0114179 | A1 | 5/2005 | Brackett et al. |
| 2005/0114283 | A1 | 5/2005 | Pearson et al. |
| 2005/0184988 | A1 | 8/2005 | Yanof et al. |
| 2005/0197860 | A1* | 9/2005 | Joffe et al. ........................ 705/2 |
| 2005/0238218 | A1 | 10/2005 | Nakamura |
| 2005/0273009 | A1 | 12/2005 | Deischinger et al. |
| 2006/0093198 | A1 | 5/2006 | Fram et al. |
| 2006/0093199 | A1 | 5/2006 | Fram et al. |
| 2006/0093207 | A1 | 5/2006 | Reicher et al. |
| 2006/0095423 | A1 | 5/2006 | Reicher et al. |
| 2006/0095426 | A1 | 5/2006 | Takachio et al. |
| 2006/0106642 | A1 | 5/2006 | Reicher et al. |
| 2006/0111941 | A1 | 5/2006 | Blom |
| 2006/0181548 | A1 | 8/2006 | Hafey |
| 2006/0230072 | A1 | 10/2006 | Partovi et al. |
| 2006/0239573 | A1 | 10/2006 | Novatzky et al. |
| 2006/0277075 | A1 | 12/2006 | Salwan |
| 2006/0282408 | A1 | 12/2006 | Wisely et al. |
| 2007/0050701 | A1 | 3/2007 | El Emam et al. |
| 2007/0055550 | A1 | 3/2007 | Courtney et al. |
| 2007/0067124 | A1 | 3/2007 | Kimpe et al. |
| 2007/0073556 | A1 | 3/2007 | Lau et al. |
| 2007/0174079 | A1 | 7/2007 | Kraus |
| 2007/0192140 | A1 | 8/2007 | Gropper |
| 2007/0239481 | A1 | 10/2007 | DiSilvestro et al. |
| 2008/0059245 | A1 | 3/2008 | Sakaida et al. |
| 2008/0103828 | A1 | 5/2008 | Squilla et al. |
| 2008/0275913 | A1 | 11/2008 | van Arragon et al. |
| 2009/0198514 | A1 | 8/2009 | Rhodes |
| 2010/0016430 | A1 | 1/2010 | Long |
| 2010/0138239 | A1 | 6/2010 | Reicher et al. |
| 2010/0198608 | A1 | 8/2010 | Kaboff et al. |
| 2010/0201714 | A1 | 8/2010 | Reicher |

| | | |
|---|---|---|
| 2011/0267339 A1 | 11/2011 | Fram |
| 2011/0316873 A1 | 12/2011 | Reicher |
| 2012/0194540 A1 | 8/2012 | Reicher |

OTHER PUBLICATIONS

Non-Final Office Action dated Aug. 28, 2007 in U.S. Appl. No. 11/179,384.
Final Office Action dated Jun. 26, 2008 in U.S. Appl. No. 11/179,384.
Non-Final Office Action dated Dec. 29, 2008 in U.S. Appl. No. 11/179,384.
Final Office Action dated Jul. 24, 2009, in U.S. Appl. No. 11/179,384.
Notice of Allowance dated Nov. 3, 2009, in U.S. Appl. No. 11/179,384.
Non-Final Office Action dated Aug. 18, 2010 in U.S. Appl. No. 12/702,976.
Interview Summary dated Dec. 1, 2010, in U.S. Appl. No. 12/702,976.
Final Office Action dated Feb. 17, 2011 in U.S. Appl. No. 12/702,976.
Interview Summary dated May 31, 2011 in U.S. Appl. No. 12/702,976.
Non-Final Office Action dated Oct. 1, 2009, in U.S. Appl. No. 11/268,261.
Notice of Allowance dated Feb. 2, 2010, in U.S. Appl. No. 11/268,261.
Notice of Allowance dated May 17, 2010, in U.S. Appl. No. 11/268,261.
Supplemental Notice of Allowance dated Aug. 6, 2010, in U.S. Appl. No. 11/268,261.
Interview Summary dated May 14, 2010, in U.S. Appl. No. 11/268,261.
Issue Notice dated Sep. 2, 2010, in U.S. Appl. No. 11/268,261.
Notice of Allowance dated Oct. 8, 2010, in U.S. Appl. No. 11/268,261.
Notice of Allowance dated Dec. 3, 2010, in U.S. Appl. No. 11/268,261.
Notice of Allowance dated Jan. 6, 2011, in U.S. Appl. No. 11/268,261.
Office Action dated May 16, 2011, in U.S. Appl. No. 12/857,915.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Interview Summary dated Nov. 16, 2010 in U.S. Appl. No. 11/265,979.
Final Office Action dated Dec. 23, 2010 in U.S. Appl. No. 11/265,979.
Interview Summary dated Mar. 17, 2011 in U.S. Appl. No. 11/265,979.
Notice of Allowance dated May 26, 2011 in U.S. Appl. No. 11/265,979.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Notice of Allowance dated Feb. 25, 2011 in U.S. Appl. No. 11/268,262.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 5, 2011 in U.S. Appl. No. 12/870,645.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Non Final Office Action dated Sep. 16, 2010 in U.S. Appl. No. 11/942,687.
Interview Summary dated Dec. 3, 2010 in U.S. Appl. No. 11/942,687.
Final Office Action, dated Apr. 5, 2011 in U.S. Appl. No. 11/942,687.
Non-Final Office Action dated Apr. 14, 2010 in U.S. Appl. No. 11/944,027.
Interview Summary dated May 13, 2010 in U.S. Appl. No. 11/944,027.
Final Office Action dated Dec. 23, 2010 in U.S. Appl. No. 11/944,027.
Interview Summary dated Mar. 31, 2011 in U.S. Appl. No. 11/944,027.
Non-Final Office Action dated Sep. 29, 2010 in U.S. Appl. No. 11/944,000.
Final Office Action dated Apr. 20, 2011 in U.S. Appl. No. 11/944,000.
Interview Summary dated Jun. 7, 2011 in U.S. Appl. No. 11/944,000.
Notice of Allowance dated Jul. 20, 2011, in U.S. Appl. No. 12/702,976.
Interview Summary dated Sep. 6, 2011, in U.S. Appl. No. 12/857,915.
Office Action dated Dec. 1, 2011, in U.S. Appl. No. 13/228,349.
Notice of Allowance dated Feb. 6, 2012, in U.S. Appl. No. 13/228,349.
Final Office Action dated Dec. 15, 2011, in U.S. Appl. No. 12/857,915.
Non-Final Office Action dated Jan. 11, 2012 in U.S. Appl. No. 13/079,597.
Office Action dated Feb. 3, 2012 in U.S. Appl. No. 12/622,404.
Mendelson, et al., "Informatics in Radiology—Image Exchange: IHE and the Evolution of Image Sharing," RadioGraphics, Nov.-Dec. 2008, vol. 28, No. 7.
Notice of Allowance dated Jul. 20, 2012, in U.S. Appl. No. 13/228,349.
Office Action dated Jun. 12, 2012, in U.S. Appl. No. 12/857,915.
Office Action dated Jun. 8, 2012 in U.S. Appl. No. 13/171,081.
Interview Summary dated Jul. 31, 2012 in U.S. Appl. No. 13/171,081.
Interview Summary dated Jun. 28, 2012 in U.S. Appl. No. 11/944,027.
Final Office Action dated Aug. 6, 2012 in U.S. Appl. No. 12/622,404.
Notice of Allowance dated Apr. 25, 2012, in U.S. Appl. No. 13/079,597.
Office Action dated Apr. 19, 2012 in U.S. Appl. No. 11/944,027.
US 7,801,341, 09/2010, Fram et al. (withdrawn)
US 8,208,705, 06/2012, Reicher et al. (withdrawn)

* cited by examiner

| Exam Receive Options-IHS Central Server | ✖ |

- ☑ Schedule an automatic receive every [5] minutes — [OK]
- ☐ Receive exams upon login — [Cancel]

Exam Copy Parameters
*Exam Components*
- ☑ Images  ☑ Montages  ☑ Voice Clips  ☑ Notes  ☐ Reports

— 302

Receivable Exam Criteria
- ☐ I am the Assigned Reading Physician
- ☐ [Modality...] [_____]
- ☐ [Acquisition Site...] [_____]
- ☑ [Exam Status...] [Unread]
- ☐ [Exam Priority...] [_____]
- ☐ Additional Filter [____▼]
- ☑ Ignore exams older than [2 weeks ▼]
- ☐ Ignore exams performed from [7:00.00 AM] to [11:00.00 PM]

Maximum number of [3] exam(s) will be received automatically. (Doesn't apply to manual receive)

After Exams Received
- ☑ Play sound [1] Times [_____] ▶ Browse
- ☐ Launch program [_____] ▶ Browse — 310 — 315
[Copy Report to EMR] [Location:] [_____] ▶ Browse
[Copy Montage > EMR] [Location:] [_____] ▶ Browse
— 320  — 325
[File Format] ☐ [HL-7 Text]  ☐ [PDF]  ☐ [other...]
— 330    — 332     — 334     — 336

SMART PLACEMENT RULES

CROSS-REFERENCE TO RELATED APPLICATIONS

This application is a continuation of U.S. application Ser. No. 11/942,674, filed Nov. 19, 2007, entitled "SMART PLACEMENT RULES," now U.S. Pat. No. 7,953,614, which claims priority under 35 U.S.C. §119(e) to U.S. Provisional Application No. 60/867,071, filed Nov. 22, 2006, each of which are hereby expressly incorporated by reference in their entirety.

BACKGROUND OF THE INVENTION

1. Field of the Invention

The invention relates to the management and placement of medical data, and more particularly to the smart placement of received medical data within an Electronic Medical Records (EMR) system, for example.

2. Description of the Related Art

Medical data is increasingly being stored in the form of digital documents that can be electronically transmitted and shared between multiple computing devices. EMR systems store various types of medical data, such as images from x-rays and MRIs, montages of images, voice clips, notes, reports, and other text, audio, and/or video from a wide variety of sources. EMR systems receive medical data from physicians or other medical practitioners, for example, that have generated and/or received the medical data from one or more imaging facilities. This medical data often needs to be viewed, manipulated, interpreted, and/or shared between multiple medical members in the same facility or members in one or more distant facility. Accordingly, there is a need for improved systems and methods for the smart placement of medical records so that collaboration among medical faculty can take place.

SUMMARY OF THE INVENTION

In one embodiment, a method of managing medical data received from at least one medical imaging facility, the medical data comprising medical images and medical reports, comprises receiving data from a user indicating a first storage location of an EMR system for storing medical images and a second storage location of the EMR system for storing medical reports received from the imaging facilities, receiving medical images and medical reports from at least one of the medical imaging facilities via one or more networks, associating each of the received medical images and medical reports with respective patients, and transferring the medical images and the medical reports to the EMR system with information indicating the first and second storage locations for the respective medical images and medical reports.

In one embodiment, a method of manipulating medical data associated with a patient comprises receiving first information from a user of a first computer specifying medical data to be retrieved by the first computer, receiving instructions comprising an indication of a secondary storage location, receiving medical data associated with a patient in response to matching the first information to certain attributes associated with the medical data, and transferring at least some of the medical data to the secondary storage location, wherein the secondary storage location is configured to associate the transferred medical data with other medical data associated with the patient so that the transferred medical data is accessible by users of the secondary storage system.

In one embodiment, a medical data management system comprises a storage device for storing received medical data associated with a patient and for storing smart placement rules indicating one or more components of medical data to be transferred to an indicated secondary storage location, and a smart placement module for identifying one or more components of the received medical data that are indicated in the smart placement rules and forwarding a copy of the identified one or more components to the secondary storage location.

In one embodiment, a method of forwarding medical data to a patient records system, the method comprises receiving rules from a user of a computing system, the rules comprising criteria indicating which components of the medical data should be transmitted from a medical image storage device to the computing system and/or when the components should be transmitted to the computing system, receiving a storage location from the user of the computing system indicating where the medical data is to be stored in a patient records system, attaching information to medical data received from the medical image storage device, the information indicating one or more storage locations in the patient record system so that respective storage locations are associated with different components of the received medical data, and transmitting the received medical data and the attached information to the patient records system.

BRIEF DESCRIPTION OF THE DRAWINGS

FIG. 3 is one embodiment of a graphical user interface that may be used to establish smart placement rules.

DETAILED DESCRIPTION OF THE CERTAIN EMBODIMENTS

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

As used herein, the terms "medical data," "medical-related data," and "medical records" are defined to include data in any format that is related to a patient. As non-limiting examples, the terms may include, but are not limited to, medical images, such as radiograph, computed tomography (CT), magnetic resonance imaging (MRI), Ultrasound (US), mammogram, positron emission tomography scan (PET), and nuclear scan (NM) images; montages of medical images; medical reports; voice clips, notes; and medical reports. Medical data may be stored in various formats, such as PDF, JPEG, GIF, PNG, DOC, XLS, PPT, MP3, WAV, HTML, XML, and various other formats.

A "component" of medical data is a category or type of medical data. For example, components of medical data may include an image component comprising medical images and a report component comprising a written report corresponding to the medical images. Components of medical data may include, for example, images, montages, voice clips, notes, and reports.

Figure 1A:
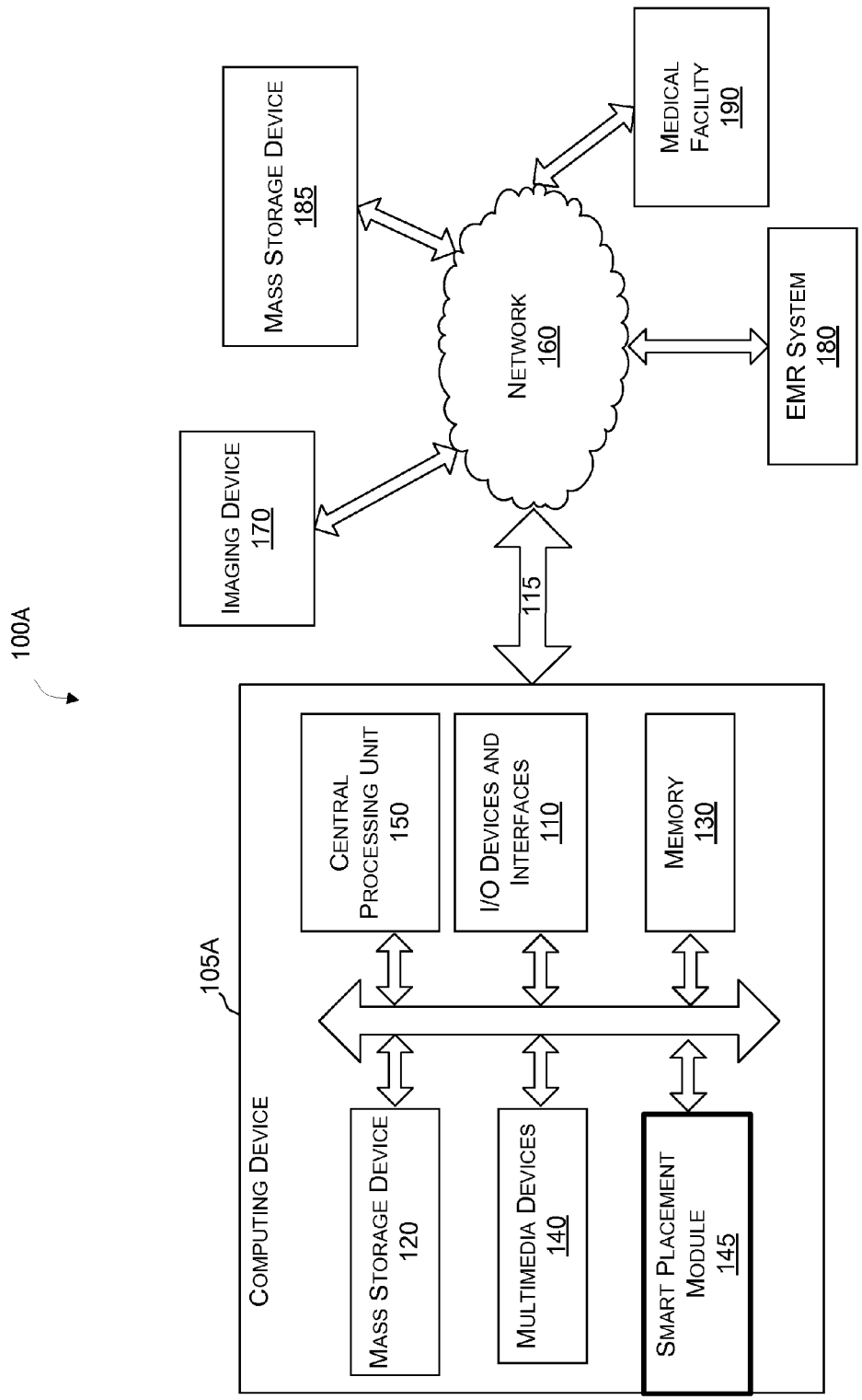
FIG. 1A is a block diagram of a computing system comprising a computing device in communication with a network and various networked devices.

FIG. 1A is a block diagram of a computing system 100A comprising a computing device 105A in communication with a network 160 and various networked devices. The computing system 100A may be used to implement certain systems and methods described herein. Depending on the embodiment, the functionality described below with reference to certain components and modules of the computing system 100A may be combined into fewer components and modules or further separated into additional components or modules.

The exemplary computing device 105 comprises a memory 130, such as random access memory ("RAM") for temporary storage of information and a read only memory ("ROM") for permanent storage of information, and a mass storage device 120, such as a hard drive, diskette, or optical media storage device. The mass storage device 120 may comprise one or more hard disk drive, optical drive, networked drive, or some combination of various digital storage systems. The computing device 105 also comprises a central processing unit (CPU) 150 for computation. Typically, the modules of the computing device 105 are in data communication via one or more standards-based bus system. In different embodiments of the present invention, the standards based bus system could be Peripheral Component Interconnect (PCI), Microchannel, SCSI, Industrial Standard Architecture (ISA) and Extended ISA (EISA) architectures, for example.

The computing device 105 is generally controlled and coordinated by operating system software, such as the Windows 95, 98, NT, 2000, XP, Vista, or other compatible operating systems. In Macintosh systems, the operating system may be any available operating system, such as Mac OS X. In other embodiments, the computing device 105 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary computing device 105A includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. According to the systems and methods described below, medical images may be stored on the computing device 105A and automatically transmitted to one or more EMR systems manipulated by the smart placement module 145 based on one or more placement rules established by a user of the computing device 105A. The computing device 105 may also include one or more multimedia devices 140, such as speakers, video cards, graphics accelerators, and microphones, for example.

In the embodiment of FIG. 1A, the I/O devices and interfaces 110 provide a communication interface to various external devices. In the embodiment of FIG. 1A, the computing device 105A is in data communication with a network 160, such as a LAN, WAN, or the Internet, for example, via a communication link 115. The network 160 may be coupled to various computing devices and/or other electronic devices. In the exemplary embodiment of FIG. 1A, the network 160 is in data communication with an imaging device 170, an Electronic Medical Record (EMR) system 180, a mass storage device 185, and a medical facility 190. Depending on the embodiment, the EMR system 180 may comprise proprietary medical record management software and/or one or more of various available third-party EMR systems. In addition to the devices that are illustrated in FIG. 1A, the network 160 may facilitate communications with other computing, imaging, and storage devices.

The imaging device 170 may be any type of device that is capable of acquiring medical images, such as MRI, x-ray, mammography, or CT scan systems. In one embodiment, the imaging device 170 is configured to store images and data associated with images. In one embodiment, the imaging device 170 communicates with the computing device 105 via the network 160, or one or more other wired and/or wireless networks, such as a secure LAN, for example. In one embodiment, the image data is stored in Digital Imaging and Communications in Medicine ("DICOM") format. The complete DICOM specifications, which may be found on the National Electrical Manufactures Association Website at <medical.nema.org>. Also, *NEMA PS 3—Digital Imaging and Communications in Medicine,* 2004 ed., Global Engineering Documents, Englewood Colo., 2004, is hereby incorporated by reference in its entirety.

The exemplary EMR system 180 is configured to store digital medical data so that doctors, medical staff, patients, and/or other authorized personnel can effectively view and share the medical data. The EMR system 180 may provide medical data from multiple sources to the computing device 105 via the network 160. Likewise, medical data from the computing device 105 may be provided to other medical facilities, such as the medical facility 190 of FIG. 1A, via the EMR system 180. Depending on the embodiment, the medical facility 190 may include one or more hospitals, clinics, doctor's offices, or any other facility that generates and/or processes medical data. The medical facility 190 may include one or more imaging devices, such as imaging devices that generate the image types described above in the definition of medical data. In one embodiment, multiple computing devices, such as the computing device 105, may be housed at the medical facility 190.

In the embodiment of FIG. 1A, the smart placement module 145 is configured to forward medical data received by the computing device 105A, such as from the imaging device 170 or the medical facility 190, to one or more EMR systems according to placement rules established by a user of the computing device 105. In one embodiment, medical data is received at the computing device 105 in response to matching of one or more auto-pull rules with particular medical data and/or components of the medical data. For example, in an auto-pull system, either the computing device 105 or a remote server may be configured to periodically select, based upon a user-defined schedule, medical data satisfying the user-specific rules. The user may be authenticated with the remote server in order to determine the user's rights to receive medical data and the selected medical data may then be transmitted to the computing device 105A so that it is locally available for the viewing physician, technician, or other authorized viewer. U.S. Pub. No. 2006/0095423, published on May 4, 2006 to Reicher et al. titled "Systems and Methods for Retrieval of Medical Data," which is hereby incorporated by reference in its entirety, describes various systems and methods for establishing auto-pull rules for selectively transferring medical data to a computing device.

In one embodiment, the smart placement module 145 determines components of received medial data to forward to one or more secondary storage locations, such as the EMR system 180 or a specific directory of a local storage device, based on smart placement rules that are established by an authorized user of the computing device 105. Although the description below refers primarily to an EMR system 180 as the secondary storage device, the systems and methods described herein are operable with any suitable secondary storage device, whether local or remote to the computing device 105.

Through the automatic application of smart placement rules by the smart placement module 145, the need for a user of the computing device 105 to manually select and transfer components of medical data to one or more secondary locations, such as the EMR system 180, is reduced or removed. Accordingly, the smart placement module 145 allows a user of the computing device 105, and other authorized computer users that are in communication with the EMR system 180, to locate data regarding a patient in the EMR system 180. In one embodiment, the smart placement module 145 provides an interface for an authorized user to establish smart placement rules that indicate what components of medical data should be forwarded to one or more secondary storage locations. In one embodiment, smart placement rules may also indicate storage locations for respective components of medical data, such as a directory on a local storage device, a directory on a shared storage device, or a folder in an EMR system, for example. Depending on the embodiment, the smart placement module 145 may be configured to copy the selected components of medical data (e.g., leaving a copy on the computing device 105) or to move the selected components of medical data (e.g., not leaving a copy on the computing device 105) to the selected secondary storage location. In one embodiment, the mass storage device 120 stores the user-specific rules. A further description of the smart placement module 145 and its processes will be discussed below.

Figure 1B:
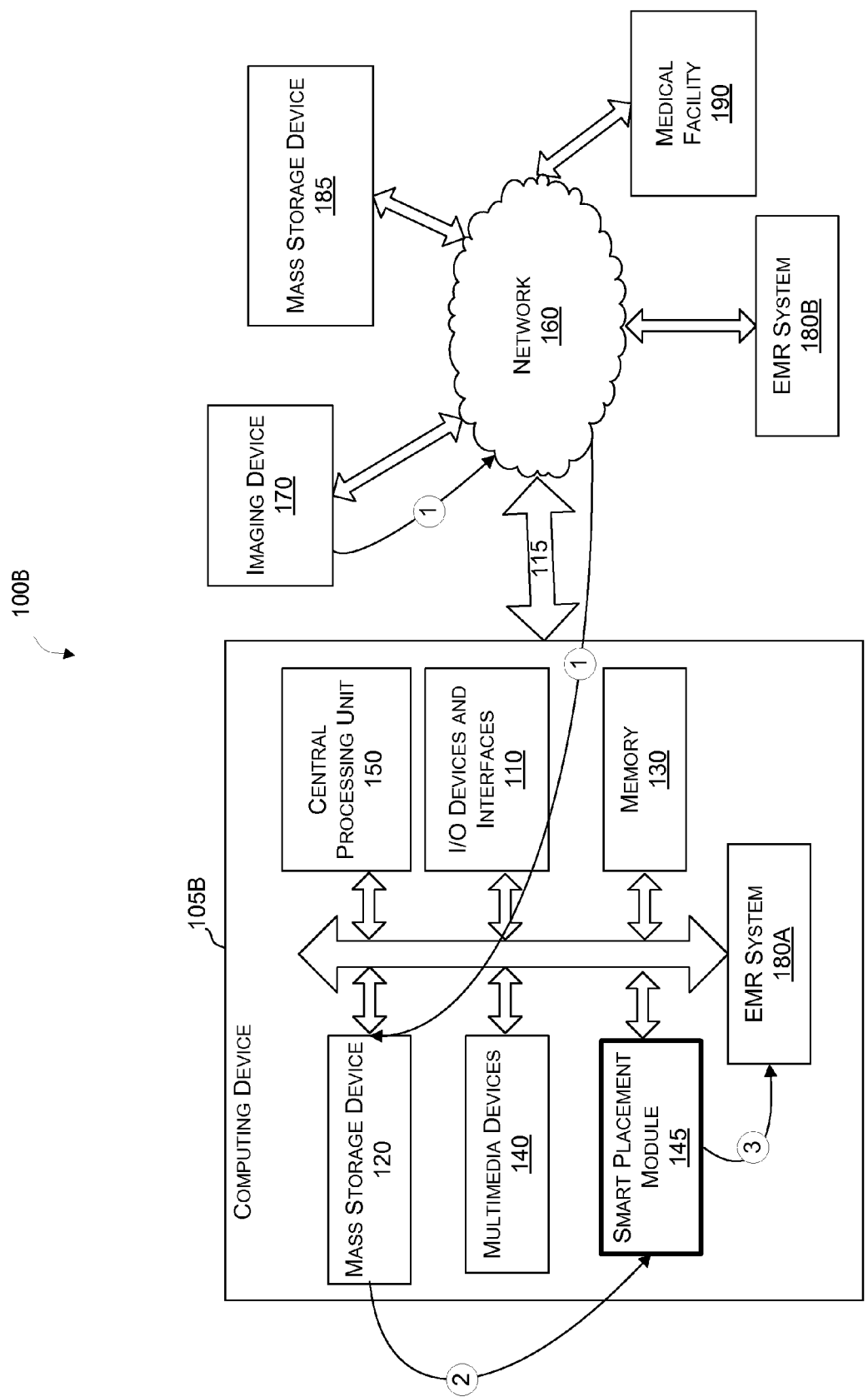
FIG. 1B is a block diagram illustrating one embodiment of a computing system comprising a computing device in communication with the imaging device via the network.

FIG. 1B is a block diagram illustrating one embodiment of a computing system 100B comprising a computing device 105B in communication with the imaging device 170 via the network 160. In the embodiment of FIG. 1B, the computing device 105B comprises a local version of the EMR system 180. In this embodiment, the EMR system 180 may be used exclusively by the computing device 105B, may be used by other devices coupled to the computing device 105B, such as via a secured local area network, and/or may be accessed by any authorized devices that are in communication with the network 160.

In the embodiment of FIG. 1B, an exemplary temporal flow of data is indicated by the circled numerals 1-3 and is described in further detail below. Depending on the embodiment, certain steps may be removed and additional steps may be added.

In step one of FIG. 1B, the imaging device 170 transmits medical data to the network 160, and the medical data, such as medical images, reports, and/or other medical information, is received and stored by the computing device 105B. In one embodiment, medical data is selected for transmission to the computing device 105B as a result of matching one or more auto-pull rules that are established by a user of the computing device 105B.

In step two, the smart placement module 145 of the computing device 105B applies smart placement rules to the received medical data. In one embodiment, the smart placement rules indicate that certain components of medical data is to be copied and/or moved to a secondary storage location either on the computing device 105B, such as in a folder of the EMR system 180, or to another device across the network 160. For example, smart placement rules may indicate that received medical data is to be transferred to a selected EMR system and associated with respective patient data on the EMR system.

In one embodiment, the smart placement rules indicate one or more components of medical data that are to be transmitted to a selected one or more destinations. For example, a user can establish placement rules indicating that only textual reports are to be transmitted to a selected EMR system, or the user can establish placement rules indicating that all components of received medical data should be transmitted to the selected EMR.

In step three of FIG. 1B, the indicated components of the received medical data are transmitted to the EMR system 180. In one embodiment, the transmitted components are associated with other medical data of the respective patient(s) at the EMR system 180. In such an embodiment, an authorized user of the EMR system 180 may access the transmitted components via the respective patient's inbox in the EMR system 180. Thus, in one embodiment the smart placement module 145 advantageously automates a process of selecting medical data for transmission to the EMR system 180 so that the medical data may be associated with other medical data associated with the patient at the EMR system 180. Additionally, the smart placement module 145 may be configured to automatically apply smart placement rules when medical data is received at the computing device 105 so that components of the medical data are quickly availably to authorized users of the EMR system, without any intervention by the user.

In one embodiment, the smart placement module 145 generates a token comprising information indicating one or more software applications associated with components of medical data that are transmitted to the EMR system 180. In one embodiment, the smart placement module 145 determines the appropriate text, graphic, audio, etc., viewer(s) that may be used to present respective data items that are transmitted to the EMR system 180. For example, if the retrieved medical data includes image files, then the token sent by the smart placement module 145 to the EMR system 180 may indicate a specific third-party software viewing application that the viewing system should launch in order to view the image files. In one embodiment, the tokens may designate a class of software application so that the user's default application of a given type of application may be selected when indicated by a token.

In one embodiment, the smart placement module 145 generates a patient ID file that is transmitted with the indicated components to the EMR system 180. The patient ID file comprises an indication of a patient name, examination date, medical record number, and/or social security number, for example, of a patient associated with the transmitted medical data components. Thus, the patient ID file is usable by the EMR system 180 to place the medical data components in locations associated with the appropriate patient, such as folders, directories, or inboxes associated with respective patients. In other embodiments, the patient ID file may comprise additional information regarding a patient.

Figure 2:
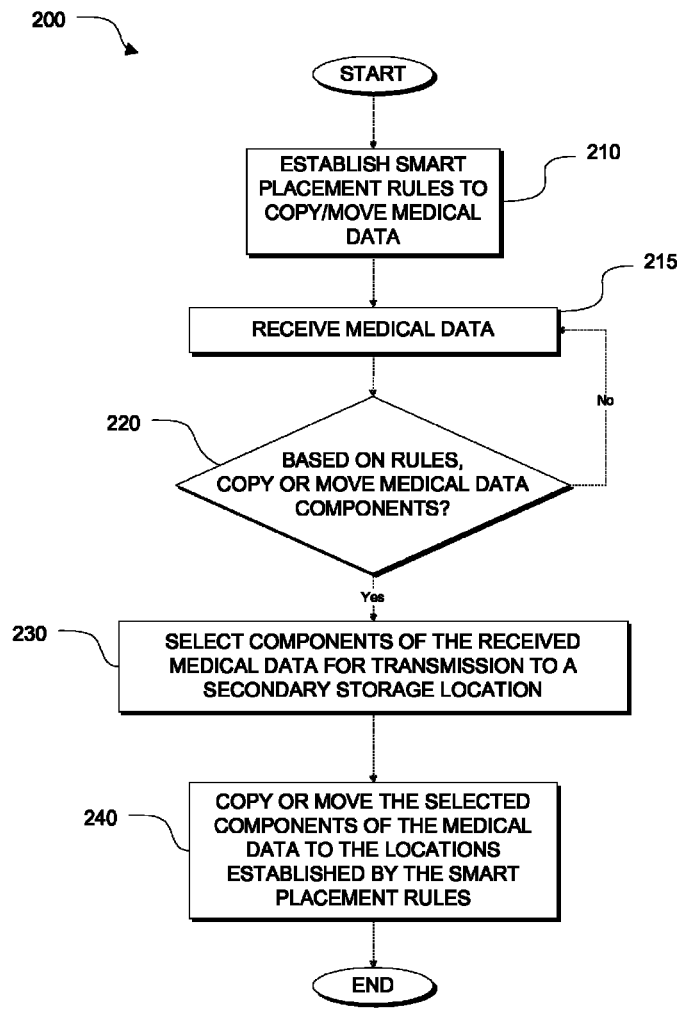
FIG. 2 is a flowchart illustrating one embodiment of a method of automatically forwarding received medical data to one or more predetermined locations based on smart placement rules.

FIG. 2 is a flowchart 200 illustrating one embodiment of a method of automatically forwarding received medical data to one or more predetermined locations based on smart placement rules. The method of FIG. 2A may be initiated in response to receiving new medical data at the computing device 105, such that the medical data is forwarded based on the smart placement rules substantially immediately after being received at the computing device 105. In other embodiments, the method of FIG. 2A is user initiated and may operate on medical data that has been stored on the computing devices or a networked device for an extended period of time. Depending on the embodiment, the flowchart of FIG. 2 may comprise fewer or more blocks and the blocks may be performed in a different order than illustrated.

Beginning in block 210, smart placement rules are established for movement or copying of medical data components to one or more secondary storage locations. In one embodiment, the smart placement rules comprise default system rules and/or user-specific rules for each user or group of users. Depending on the embodiment, the smart placement rules may include component criteria that must be matched by received medical data in order to trigger an associated smart placement action. For example, a smart placement rule may specify that only an image and report component of medical data is to be transmitted to a particular EMR system. Thus, when new medical data is received, only the image and report components are transmitted to the EMR system. In one embodiment, the smart placement rules indicated separate storage locations for respective medical data components, such as a first location for medical images and a second location for reports. Additionally, in some embodiments, the smart placement rules indicate a format that medical data components should be in prior to transferring to the EMR system, such as HL-7 text format, or PDF format, for example.

In one embodiment, the smart placement rules may also include criteria associated with header data of certain medical data components, such as time of day and/or date that a component is received by the computing device 105, a referring physician's name, a radiologist name, an exam type, an exam modality, and various other attributes of a components. In one embodiment, default system rules are applied to received medical data if user-specific rules have not been established. FIG. 3, which is described in further detail below, illustrates an exemplary user interfaces for establishing smart placement rules.

Moving to block 215, medical data is received at the computing device 105. As noted above, the medical data may be received from any suitable computing device that is in communication with the computing device 105, such as via the network 160. As defined above, the medical data may comprise one or more of multiple files of various formats and may include various information regarding a patient. In one embodiment, the medical data is stored in the mass storage system 120 of the computing device 105.

Next, in decision block 220 the computing device 105 applies the smart placement rules to the received medical data in order to determine which components of the medical data, if any, should be copied and/or moved to one or more local or remote secondary storage locations. If a smart placement rule matches one or more components of the medical data, the method continues to block 230. If no smart placement rules match with the medical data, the method returns to block 210 where medical data from another exam, another imaging source, and/or associated with another patient is received.

At block 230, the components of the medical data indicated by the placement rules are selected for transmission to the location indicated in the matching smart placement rule. As noted above, all components may be transmitted to a single location, e.g., a folder on a local or networked storage device or a local or networked EMR system, or the smart placement rules may indicate separate storage locations for respective components of the medical data.

Moving to block 240, the computing device 105 transmits the selected components to the location or locations associated with the matched smart placement rules. As noted above, in one embodiment a patient ID file indicating one or more attributes of the patient associated with the medical data components is also transmitted to the indicated secondary location. The patient ID file may be used, for example, by the EMR system in associating the transmitted medical data components with other medical data of respective patients. In this embodiment, the medical data of the patient is quickly made available to authorized users of the EMR system by accessing the patient's records stored by the EMR system.

In one embodiment, the smart placement module 145 generates one or more tokens that are associated with specific components of the transmitted medical data. The tokens comprise information regarding compatible and/or preferred software applications that may be launched in order to view and/or hear an associated medical data component. For example, if the selected medical data comprises a series of CT scan images, a token may be generated to indicate one or more software applications in which the CT images may be viewed. Likewise, a token indicating one or more software application in which a textual report may be viewed may be associated with a textual report component. In one embodiment, the EMR system 180 may display a link and/or icon associated with a token that may be selected by a user of the EMR system 180 in order to access the corresponding medical data in an appropriate software application. Certain tokens may comprise executable software code that launches a desired software application and opens selected medical data components in the software application. For example, an authorized user of the EMR system 180, such as a user of the computing device 105 or another computing device in communication with the network, may select a link associated with a token in order to invoke execution of the token, and subsequent launching of an indicated software application and opening of the corresponding medical data.

In one embodiment, the EMR system comprises separate patient inboxes wherein some or all of the patient's medical records are stored. In general, a patient's inbox is a location and/or index of locations where the patient's medical data is stored. This method may increase privacy of the medical data for specific patients by only allowing the patient, the patient's doctor, and/or other authorized users to access the patient's medical data.

FIG. 3 is one embodiment of a graphical user interface 300 that may be used to establish smart placement rules. Depending on the embodiment, the layout of the graphical user interface, the types of input fields, buttons, and checkboxes may be modified. The exemplary graphical user interface 300 comprises a component selection pane 302 that allows a user of the computing device 105, for example, to indicate which components of received medical data should be forwarded to one or more indicated secondary storage locations. In the embodiment of FIG. 3, check boxes for component types images, montages, voice clips, notes, and reports are provided, where a particular component is selected for transferring to an indicated secondary location if the corresponding checkbox is selected. In other embodiments, other controls may be used in order to allow a user to select one or more components. In other embodiments, fewer or additional components may be available for selection.

The exemplary user interface of FIG. 3 also comprises smart placement pane 305 that allow a user to select secondary storage locations for report and/or montage components of medical data. In the embodiment of FIG. 3, the smart placement pane 305 comprises a report copy button 310 that may be selected to indicate that received medical reports should be automatically transmitted to an EMR system, or other storage location, identified in field 315. Similarly, a montage copy button 320 may be selected in order to indicate that received montages should be automatically transmitted to an EMR system, or other storage location, identified in field 325.

In one embodiment, the smart placement module detects an EMR system that is used by the computing device and automatically populates fields 315, 325 with an indication of the detected EMR system(s). Where multiple EMR systems are detected, the text display fields 315, 325 may comprise dropdown fields that allow the user to select one or more of the EMR systems to which the medical data should be transmitted. In one embodiment, the user is provided with a directory structure that may be navigated in order to locate and select an EMR system or another storage location. In one embodiment, after establishing the smart placement rules, such as using the interface of FIG. 3, when medical data is received by the computing device 105, the components of the medical data indicated in the component selection pane 302 are automatically forward to the locations indicated in the smart placement pane 305.

The exemplary smart placement pane 305 further comprises buttons 332, 334, and 336 that allow the user to select a desired format for the medical data that is transmitted to the indicated EMR system. In the embodiment of FIG. 3A, HL-7 text format may be selected by selecting button 332 and PDF format may be selected by selecting button 334. In one embodiment, when button 332 is selected, medical data is converted into the Health Level 7 standard format, which is a widely known standard and format for medical records, before transmitting to the selected EMR system. Similarly, when button 334 is selected, medical data is converted into one or more Adobe PDFs before transmitting to the selected EMR system. The smart placement pane 305 further comprises an other button 336 that allows the user to select other formats for the medical data. In one embodiment, when the button 336 is selected, another user interface comprising additional data formats, such as DOC or RTF, for example, is presented to the user.

The foregoing description details certain embodiments of the invention. It will be appreciated, however, that no matter how detailed the foregoing appears in text, the invention can be practiced in many ways. For example, the above-described auto-retrieve may be performed on other types of images, in addition to medical images. For example, images of circuit boards, airplane wings, and satellite imagery may be analyzed using the described systems. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method comprising:
    accessing, by a computing system, user-defined rules for storing medical data, wherein the user-defined rules are defined by a user and the user-defined rules indicate at least:
        which types of medical data should be transmitted from medical data storage devices to a secondary medical data storage system, wherein the types of medical data include at least one or more of medical images or medical reports, and
        locations in the secondary medical data storage system associated with respective types of medical data;
    for respective pieces of medical data:
        determining, by the computing system, based on the user-defined rules and type of the piece of medical data, whether the piece of medical data should be transmitted to the secondary medical data storage system; and
        in response to determining that the piece of medical data should be transmitted to the secondary medical data storage system:
            generating information indicating a location where the piece of medical data should be stored in the secondary medical data storage system, the information comprising a token including location data or location data that is added into the piece of medical data; and
            transmitting the piece of medical data and the generated information to the secondary medical data storage system.

2. The method of claim 1, further comprising:
    wherein the token includes an indication of one or more software applications that are suitable for viewing the piece of medical data.

3. The method of claim 1, further comprising
    for respective pieces of medical data or for respective groups of pieces of medical data each related to a common patient, the generated information indicates at least one of a patient name, examination date, medical record number, or social security number.

4. The method of claim 1,
    wherein the token includes an indication of a class of software application that is suitable for viewing the piece of medical data.

5. The method of claim 1, wherein pieces of medical data comprise one or more of images, montages, reports, audio, or notes.

6. The method of claim 1, wherein the secondary medical data storage system comprises an electronic medical records system, a storage device local to the user, or a storage device that is shared with multiple users.

7. The method of claim 1, wherein locations in the secondary medical data storage system comprise respective folders, directories, or inboxes.

8. The method of claim 1, wherein locations in the secondary medical data storage system comprise locations associated with specific patients.

9. The method of claim 1, wherein the method is initiated in response to receiving medical data at the computing system.

10. The method of claim 1, wherein the user-defined rules indicate respective formats for various types of medical data.

11. A computing system comprising:
    one or more processors configured to execute instructions in order to cause the computing system to
        access user-defined rules for retrieving and storing medical data, wherein the user-defined rules are defined by a user and the user-defined rules indicate at least
            one or more types of medical data that should be transmitted to one or more secondary storage system, wherein the types of medical data include at least one or more of medical images or medical reports; and
            one or more secondary storage systems to which respective of the one or more types of medical data should be transmitted;
    for respective medical data,
        identifying, by the computer system, a component of the medical data included in the medical data;

determining whether the identified component of the medical data should be transmitted to one or more secondary storage systems based on the user-defined rules and a type of the identified component of the medical data; and in response to determining that the identified component of the medical data should be transmitted to one or more secondary storage systems, transmitting the identified component of the medical data to a secondary storage system associated with the type of the identified component of medical data indicated in the user-defined rules.

12. The computing system of claim 11, wherein the secondary storage systems are selected from the group comprising an electronic medical records system, a storage device local to the user, or a storage device that is shared with multiple users.

13. The computing system of claim 11, wherein the user-defined rules indicate a first secondary storage location for a first type of medical data and a second secondary storage location for a second type of medical data.

14. The computing system of claim 13, wherein the first secondary storage location comprises an electronic medical records system and the second secondary storage location comprises one or more of a storage device local to the user or a storage device that is shared with multiple users.

15. The computing system of claim 13, wherein the types of medical data include one or more of medical images, montages, voice clips, notes, and reports.

16. The computing system of claim 13, wherein the user-defined rules indicate one or more required attributes of components of medical data, wherein components of medical data are not transmitted to the corresponding secondary storage system unless the component is associated with the required attributes.

17. The computing system of claim 16, wherein the required attributes indicate one or more of one or more modalities, one or more acquisition sites, one or more exam statuses, one or more exam priorities, or a time period.

18. The computing system of claim 16, wherein the required attributes indicate that only components of medical data that have not previously been marked as read should be transmitted to the corresponding one or more secondary storage location.

* * * * *